United States Patent [19]
Ito

[11] Patent Number: 5,190,558
[45] Date of Patent: Mar. 2, 1993

[54] METHOD OF ELIMINATING STRATUM CORNEUM FROM THE SKIN AND AN INSTRUMENT TO BE USED THEREFOR

[75] Inventor: Narushi Ito, Tokyo, Japan

[73] Assignee: NEC Corporation, Tokyo, Japan

[21] Appl. No.: 610,057

[22] Filed: Nov. 7, 1990

[30] Foreign Application Priority Data

Nov. 8, 1989 [JP] Japan ................................ 1-288820
Mar. 19, 1990 [JP] Japan ............................... 2-28311[U]

[51] Int. Cl.$^5$ .............................................. A61B 19/00
[52] U.S. Cl. ..................................... 606/131; 604/289; 604/307
[58] Field of Search ............... 606/131, 132, 133, 134; 604/289, 290, 303, 307, 308; 156/579; 424/449

[56] References Cited

U.S. PATENT DOCUMENTS

| | | | |
|---|---|---|---|
| 2,819,717 | 1/1958 | Kugler et al. | 606/132 |
| 3,138,512 | 6/1964 | Partin | 156/579 |
| 3,487,916 | 1/1970 | Moroni et al. | 606/131 |
| 3,910,284 | 10/1975 | Orentreich | 606/131 |
| 4,455,146 | 6/1984 | Kanjinoda et al. | 604/304 |
| 4,668,228 | 5/1987 | Bolton et al. | 604/307 |
| 5,028,431 | 7/1991 | Franz et al. | 428/448 |

*Primary Examiner*—Stephen C. Pellegrino
*Assistant Examiner*—Glenn Dawson
*Attorney, Agent, or Firm*—Leydig, Voit & Mayer

[57] ABSTRACT

Pretreatment of eliminating stratum corneum form the skin for non-invasive measurement of biomedical substances in blood has been improved as to time required, pain to man for test, stability of extraction and invasion to the skin, by introducing chemical and/or steam-spraying treatment(s) of the skin to swell and/or decompose keratinized cells and/or an adhesive strength detector to monitor the elimination level.

4 Claims, 3 Drawing Sheets

FIG. 1
FIG. 2
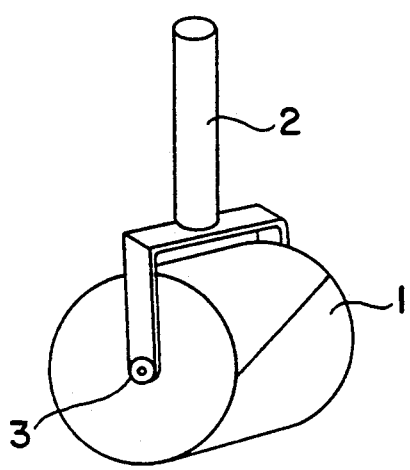
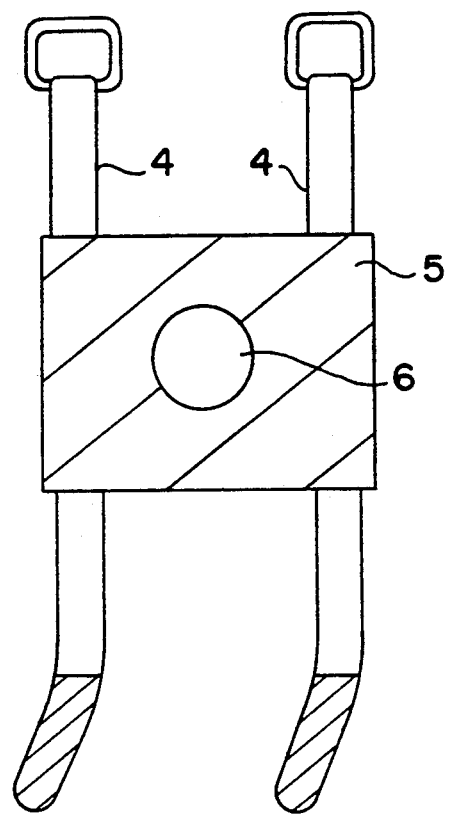
FIG. 3
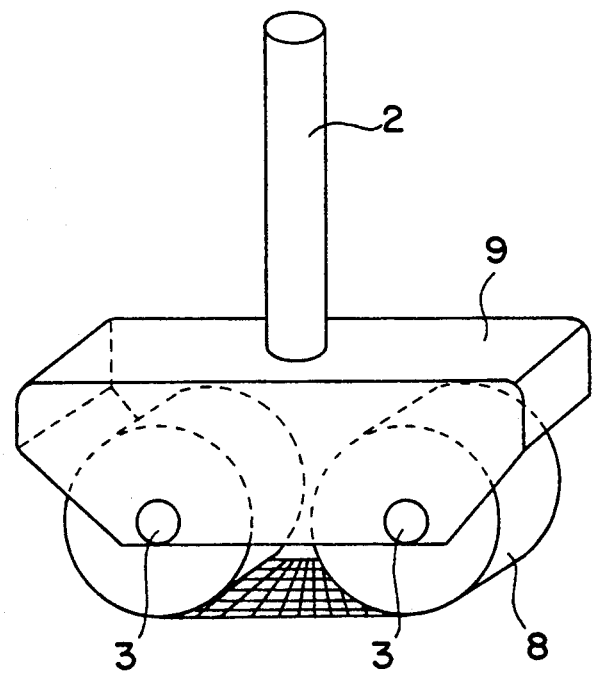

METHOD OF ELIMINATING STRATUM CORNEUM FROM THE SKIN AND AN INSTRUMENT TO BE USED THEREFOR

BACKGROUND OF THE INVENTION

1. Field of the Invention

The present invention relates to a method of eliminating stratum corneum from the skin by applying and then removing an adhesive tape to and from the skin surface as a pretreatment for non-invasive measurement of biomedical substances in blood.

2. Description of the Prior Art

In general, measurements of biomedical substances in blood are carried out by analyzing blood samples taken out from human bodies by clinical examination procedures or by biochemical automatic analyzers. Recently, however, a new measurement method using a suction effusion fluid in place of blood was reported, in "Proceeding of the first Pan Pacific Symposium, Vancouver, Canada" July 23-27, 1986, pp 57-58 and "Proceeding of the Symposium on Chemical Sensors", PV 87-9, pp 327-333.

The suction offusion fluid is a small amount of fluid obtainable by subjecting stratum-corneum-climinated skin to suction by weak evacuation and is thought of as an interstitial fluid in subcutaneous tissues or a vacuum filtrate from capillary walls. Such suction effusion fluid has merits that it has a protein concentration lower than blood and so fouling by protein of sensor surface can be reduced. Further, the suction effusion fluid is collected transcutaneously without using injectors and so psychological pain to man for test is reduced and there is also an advantage from the viewpoint of prevention of infection.

In order to collect the suction effusion fluids, however, it was required to subject the skin surface to a pretreatment of eliminating stratum corneum therefrom for facilitating extraction of the effusion fluid toward the skin surface. Heretofore, the elimination of stratum corneum was carried out by a stripping treatment which comprised application and removal of a strong adhesive tape to and from the skin of man for test repeatedly.

In such elimination method, however, there were some problems owing to the fact that it completely relied upon manual operations and so it was difficult to determine the optimum level of elimination. Any insufficient elimination would give too small amount of effusion fluid to carry out measurements and any excess elimination would cause bleeding from capillary and give pain to man for test. In short, in order to determine optimum level of elimination, very careful and long time pretreatment by an expert was required.

SUMMARY OF THE INVENTION

An object of the present invention is therefore to solve the above problems of the prior art, that is, to shorten the time required for the pretreatment, reduce the pain of man for test, stabilize the amount of effusion fluid obtainable by subsequent suction treatment and further avoid unnecessary excess invasion to the skin.

In one aspect of the present invention, before and/or at the time of applying the adhesive tape, the skin surface is subjected to a chemical treatment and/or a steam-spraying treatment so that the keratinized cells of the skin surface may be swelled and/or decomposed. By this, the elimination of stratum corneum by the adhesive tape is facilitated and so the time required for the elimination is shortened and the pain of man for test is reduced.

In another aspect of the present invention, the adhesive tape which may contain a keratolytic agent for swelling and/or decomposing keratinized cells of the skin surface is wound on a roller and rolled on the skin surface. By this, the elimination of stratum corneum by the adhesive tape can be carried out simply by rolling and thus the elimination is facilitated.

In still another aspect of the present invention, adhesive strength between the skin and the adhesive tape is detected by an adhesive strength detector. Since the adhesive strength between the skin and the adhesive tape is much increased when stratum corneum is eliminated and stratum granulosum appears on the skin surface, it becomes possible by such detector to monitor the elimination level and realize uniform elimination at the optimum level.

Thus the present invention provides a method of climinating stratum corneum from the skin by applying and then removing an adhesive tape to and from the skin surface as a pretreatment for non-invasive measurement of biomedical substances in blood, wherein before and/or at the time of applying the adhesive tape, the skin surface is subjected to a chemical treatment and/or a stream-spraying treatment so that the keratinized cells of the skin surface may be swelled and/or decomposed.

The present invention provides also an instrument for eliminating stratum corneum from the skin comprising a roller on which an adhesive tape containing a keratolytic agent for swelling and/or decomposing keratinized cells of the skin surface is wound and a grip for holding the roller.

The present invention provides further an instrument for eliminating stratum corneum from the skin comprising a roller on which an adhesive tape is wound, means for spraying steam and a body which supports said steam-spraying means and forms a grip for holding the roller.

The present invention provides further a disposable elimination tape unit for eliminating stratum corneum from the skin comprising an adhesive tape portion, a non-adhesive tab portion attached to the adhesive tape portion in the form of a tab and a fragile portion which is provided in the non-adhesive tap portion or between the adhesive tape portion and the non-adhesive tab portion and is fragile enough to be cut or deformed when a stress given thereto exceeds a certain level.

The present invention provides further an instrument for eliminating stratum corneum from the skin comprising a roller on which an adhesive tape is wound, a grip for holding the roller and an adhesive strength detector for detecting adhesive strength between the skin and the adhesive tape provided in the grip.

BRIEF DESCRIPTION OF THE DRAWINGS

FIG. 1 shows a perspective view of an embodiment of the instrument for eliminating stratum corneum from the skin according to the present invention.

FIG. 2 shows a plan view of an auxiliary instrument usable in combination with the instrument according to the present invention, for defining an area of the skin where stratum corneum is to be eliminated.

FIG. 3 shows a perspective view of another embodiment of the instrument for climinating stratum corneum from the skin according to the present invention.

DESCRIPTION OF THE PREFERRED EMBODIMENTS

Figure 4A:
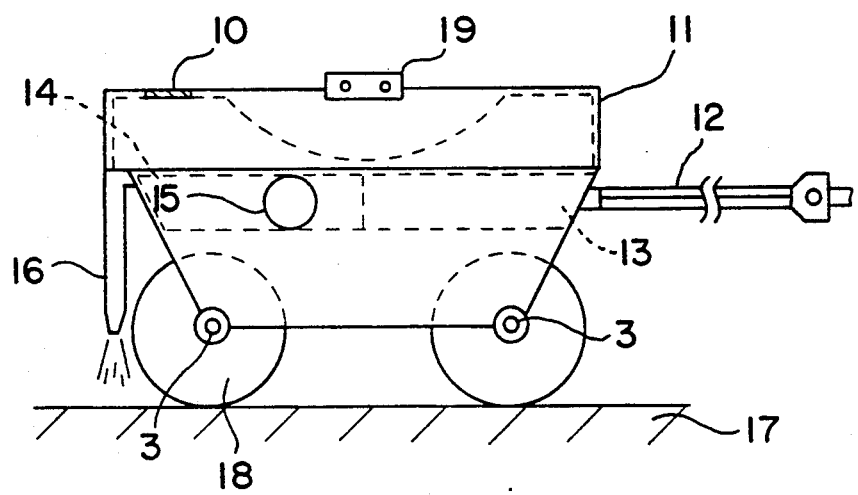
FIGS. 4a and 4b respectively show front view and plan view of still another embodiment of the instrument for eliminating stratum corneum from the skin according to the present invention.

The present invention will be explained below further in detail with respect to its some embodiments shown as working Examples.

EXAMPLE 1

In an embodiment shown in FIG. 1, an instrument for eliminating stratum corneum from the skin is prepared from an adhesive tape roller 1, a grip 2 and a shaft 3. The adhesive tape roller 1 comprises a roller on which an adhesive tape containing a keratolytic agent for swelling and/or decomposing keratinized cells of the skin surface, such as for example, salicylic acid, urea compounds, enzymes such as keratinase, is wound. The adhesive tape should preferably be sterilized. The roller 1 is rotatably supported by U-form arm portion of the grip 2 by means of a shaft 3.

In application, the roller 1 is rolled on the skin with its adhesive tape in contact with the skin surface. By the merit that fresh surface of the adhesive tape is continuously applied to the skin surface, elimination of stratum corneum can be carried out rapidly and smoothly. If a large amount of keratinized cells are attached to the adhesive tape and so the adhesive strength between the adhesive tape and the skin and the effect of the keratolytic agent become too weak, it is possible to peel off the outermost layer of the adhesive tape wound on the roller thereby to revel the inner fresh layer of the adhesive tape. It is also possible to replace the entire adhesive tape roller by a new one, simply without above peeling off or after all layers of the adhesive tape are exhausted by peeling off.

FIG. 2 shows an auxiliary instrument for use in combination with the instrument of FIG. 1. This auxiliary instrument comprises two belts 4 each having fastening devices at its end portions and a sheet 3 being attached to the belts 4 at their middle portions and having an opening 6. The auxiliary instrument is used by fixing it to human body by the bolts 4 so that an area of the skin where stratum corneum should be eliminated may be exposed through the opening 6 but an area of the skin to be protected against elimination of stratum corneum may be covered with the sheet 5. By such auxiliary instrument, it becomes possible to selectively pretreat only selected necessary area of the skin by the instrument for eliminating stratum corneum.

EXAMPLE 2

In FIG. 3, another embodiment of the instrument for eliminating stratum corneum from the skin according to the present invention is shown. In this embodiment, two rollers 8 are rotatably supported by a U-form arm portion 9 of a grip 2 by means of two shafts 3, respectively. An adhesive tape, which should preferably be sterilized and contain a keratolytic agent as in Example 1, is wound on these two rollers 8 to run from one to the other when the two rollers are rolled on the skin surface. By such embodiment, an additional merit that a longer adhesive tape can be used without manual peeling off or frequent replacement of rollers in comparison with the embodiment of Example 1 can be obtained. It is also possible to use the auxiliary instrument as shown in FIG. 2 in combination with the elimination instrument of this embodiment.

EXAMPLE 3

Figure 4B:
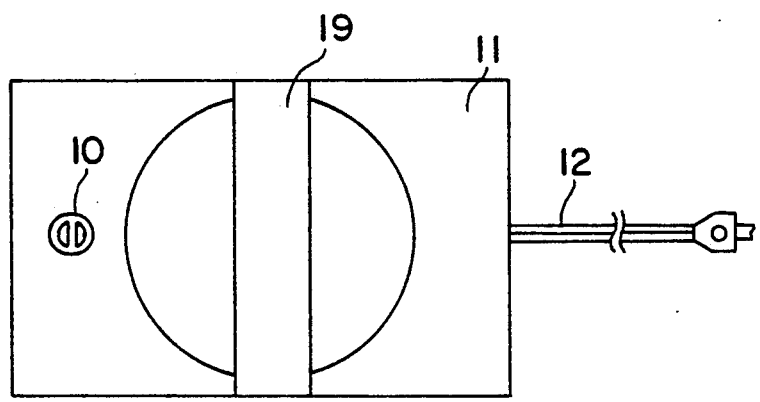

In FIGS. 4a and 4b, still another embodiment of the instrument for eliminating stratum corneum from the skin according to the present invention is shown. In this embodiment, a water tank 11 with a water inlet 10, an electronic steam generator 14 with an electric source 13 and an electric cord 12, an electric fan 15 and a steam nozzle 10 are provided to constitute means for spraying steam. These are supported by a body 19, a portion of which forms a grip for holding the roller. Two rollers 18 are rotatably supported by the body 19 by means of two shafts respectively and an adhesive tape is wound on them as in the above Example 2.

In application, steam is generated by the generator 14, blown by the fan 15 and sprayed by the nozzle 16 to the skin surface 17, as the rollers are rolled on the skin surface 17. By this, an additional merit of swelling keratinized cells before elimination thereof can be obtained. Similarly to Examples 1 and 2, it is possible to used an adhesive tape containing a keratolytic agent or to use an auxiliary instrument shown in FIG. 2 in combination with the stratum corneum elimination instrument.

EXAMPLE 4

Figure 5:
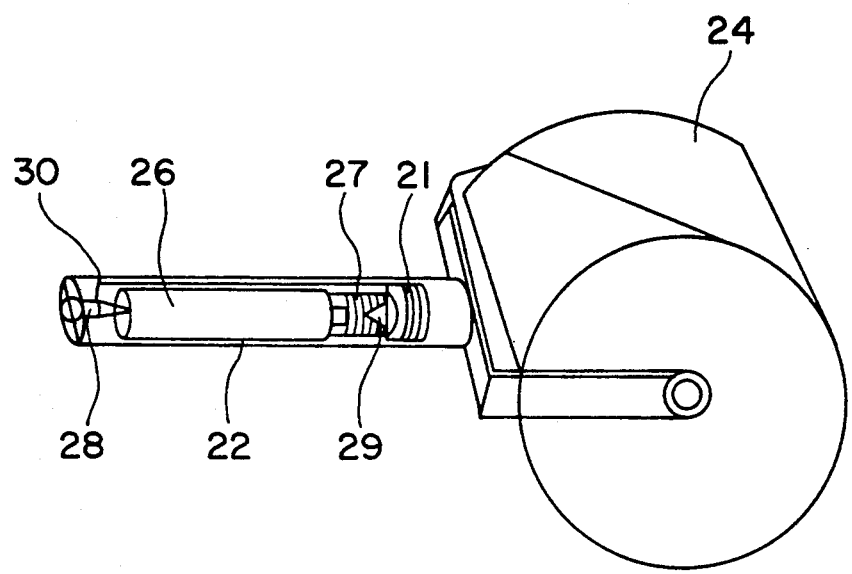
FIG. 5 shows a perspective view of still another embodiment of the instrument for eliminating stratum corneum from the skin according to the present invention, wherein a part is cut out to show inner constitution.

In FIG. 5, an instrument similar to the stratum elimination instrument of Example 1 is shown. In the instrument of FIG. 5, an adhesive strength detector for detecting adhesive strength between the skin and the adhesive tape is provided in a grip 22. The detector comprises a battery 26, a strain setting spring 27, a lamp 28, a contact point 29, a cord 30 and a guide 21. Although the illustrated adhesive strength detector is shown incorporated in an instrument similar to that described in example 1, an adhesive strength detector may be provided in any of the embodiments of the present invention.

In application, an adhesive tape roller 24 is rolled on the skin surface by pushing the grip 22 in parallel with the skin surface to apply strain corresponding to the adhesive strength between the skin and the adhesive tape to the strain setting spring 27. As keratinized cells are eliminated, the adhesive strength and accordingly the corresponding strain to the spring 27 are increased. When the strain to the spring 27 reaches a previously set value, the spring 27 is compressed enough to let the contact point 29 contact with battery 26 so that the lamp 28 may be turned on by a current flowing through the code 30. It is possible to determine the end of elimination of keratinized cells, by frequent lighting of the lamp 28. By this, it becomes possible to monitor the elimination level and realize uniform elimination at the optimum level.

EXAMPLE 5

Figure 6:
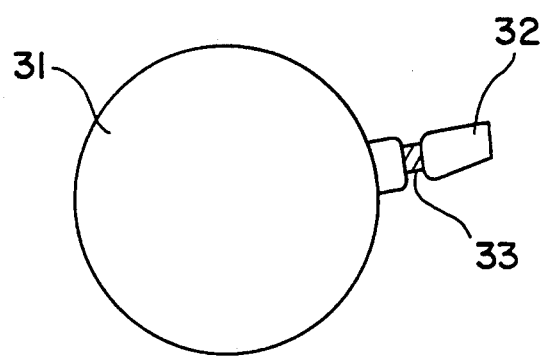
FIG. 6 shows a front view of an embodiment of the disposable elimination tape unit for eliminating stratum corneum from the skin according to the present invention.

In FIG. 6, a disposable elimination tape unit for eliminating stratum corneum from the skin is shown. This unit comprises a circular adhesive tape portion 31, a non-adhesive tab portion 32 attached to the adhesive tape portion 31 and a fragile thin or narrow tape portion 33 provided in the middle of the tab portion 32.

In application, the adhesive tape portion 31 is applied to the skin surface and removed by pulling the tab portion 32. After keratinized cells are eliminated by repeating such operation, the adhesive strength between the skin and the adhesive tape portion 31 will be increased and correspondingly the strain acting on the fragile tape portion 33 will be increased. By setting the strength against tearing or deformation of the fragile tape portion 33 to an appropriate level, it becomes possible to determine the end of elimination of keratinized cells.

The fragile tape portion 33 can be placed between the adhesive tape portion 31 and the tap portion 32. In this case, it is preferable to attach another tab portion to the adhesive tape portion 31 so that removal of the adhesive tape portion 31 may be facilitated. Similarly to Examples 1 and 2, it is possible to use an adhesive tape containing a keratolytic agent in the adhesive tape portion 31.

In the above Examples 1-3, the time required for the elimination of stratum corneum from the skin could be shortened to an extent of 5 min. in comparison with at least 20 min. required by the conventional method and the pain of man for test could be much reduced.

In the above Examples 4-5, additional merits could be obtained, that is, the amount of effusion fluid obtainable by subsequent suction treatment could easily be stabilized and unnecessary excess invasion to the skin could easily be avoided, as shown in the following table 1:

TABLE 1

| Man for Test | According to Examples 4 and 5 | | Conventional method | |
|---|---|---|---|---|
| | AEF | IS | AEF | IS |
| 1 | B | a | A | c |
| 2 | B | b | A | c |
| 3 | A | a | A | c |
| 4 | A | a | A | b |
| 5 | A | a | A | c |

AEF . . . Amount of Effusion Fluid
A: more than 0.2 ($\mu l \cdot cm^{-2} \cdot min^{-1}$)
B: 0.1-0.2
C: less than 0.1
IS . . . Invasion to Skin
a: no invasion observed
b: weak redness observed
c: strong redness observed

I claim:

1. An instrument for eliminating stratum corneum from the skin comprising a roller on which an adhesive tape is wound, means for spraying steam and a body which supports said steam-spraying means and forms a grip for holding the roller, whereby the steam spraying means applies steam to the skin to swell keratinized cells prior to their removal by said adhesive tape.

2. The instrument according to claim 1, further comprising an adhesive strength detector for detecting adhesive strength between the skin and the adhesive tape provided in the body.

3. The instrument according to claim 1, wherein the adhesive tape contains a keratolytic agent for swelling and/or decomposing keratinized cells on the skin surface.

4. A disposable elimination tape unit for eliminating stratum corneum from the skin comprising; an adhesive tape portion containing a keratolytic agent for swelling and/or decomposing keratinized cells of the skin surface, and a non-adhesive tab portion attached to the adhesive tape portion in the form of a tab and a fragile portion, said fragile portion being provided in the middle of the tab, or between the adhesive tape portion and the tab, and having a predetermined strength wherein the fragile portion will tear or deform when a stress given thereto exceeds a certain level indicative of the elimination of said keratinized cells.

* * * * *